United States Patent [19]
Ashby

[11] Patent Number: 5,578,010
[45] Date of Patent: Nov. 26, 1996

[54] MULTIPLE LUMEN CATHETER AND METHOD OF CONSTRUCTION

[75] Inventor: Mark P. Ashby, Laguna Niguel, Calif.

[73] Assignee: Applied Medical Resources Corporation, Laguna Hills, Calif.

[21] Appl. No.: 414,299

[22] Filed: Mar. 31, 1995

[51] Int. Cl.$^6$ .................................................. A61M 29/00
[52] U.S. Cl. .............................. 604/96; 604/43; 604/280; 604/283
[58] Field of Search ................................. 604/96, 43, 44, 604/45, 280, 283, 284, 905, 49, 264

[56] References Cited

U.S. PATENT DOCUMENTS

| | | | |
|---|---|---|---|
| 4,085,185 | 5/1978 | Adair. | |
| 5,059,170 | 10/1991 | Cameron | 604/280 X |
| 5,380,276 | 1/1995 | Miller et al. | 604/43 X |
| 5,397,306 | 3/1995 | Nobuyoshi et al. | 604/96 |
| 5,403,291 | 4/1995 | Abrahamson | 604/280 |
| 5,405,329 | 4/1995 | Durand | 604/43 X |

*Primary Examiner*—John D. Yasko
*Attorney, Agent, or Firm*—Richard L. Myers

[57] ABSTRACT

The multiple lumen catheter of this invention has a tubular member with a flexible cylindrical wall, the member comprising an outer and inner tubular body forming multiple lumens within the tubular member, an opening in the wall of the outer tubular body, an inflatable member attached to the distal end portion of the tubular member and covering the opening in the outer tubular body, and a bushing disposed between the outer and inner tubular bodies within the outer lumen in the tubular member, said bushing having an aperture surrounding the opening, and said aperture creating a channel from the outer lumen through the bushing, through the outer tubular body, and to the interior surface of the inflatable member. Also disclosed is a method of constructing the catheter. The bushing used in the construction of the catheter is also disclosed.

19 Claims, 4 Drawing Sheets

MULTIPLE LUMEN CATHETER AND METHOD OF CONSTRUCTION

BACKGROUND OF THE INVENTION

This invention relates to catheters designed for insertion into bodily cavities of living beings, and more particularly to a new and improved design for multiple lumen diagnostic or therapeutic catheters.

The invention also relates to a method of constructing the catheter by assembling the outer and inner sleeves of the catheter, the balloon affixed to the outer sleeve, and a novel construction for a bushing which is positioned between the outer and inner sleeves of the catheter, in such a manner that the tip of the catheter is sealed more effectively and reliably than possible by other prior art construction methods.

Finally, the invention relates to a novel design for the bushing which is used in the construction, and which comprises part of the design, of the novel catheter.

Catheters are frequently used in conducting diagnostic and therapeutic procedures in bodily conduits. The catheter can be used to examine the conduits by injecting dye or similar detectable fluid into the conduit. The catheter can also be used to perform angioplasty procedures to widen the lumen of a coronary artery by inflating a balloon at the catheter tip, after it has been correctly positioned in an artery, thereby compressing stenotic lesions present within the artery. In addition to balloon catheters, laser catheters, other atherectomy catheters, and various diagnostic device catheters can also be used.

A typical angiographic or angioplasty procedure comprises inserting a catheter guided by a guidewire or other guiding means into the femoral artery of the patient, followed by a dilating balloon catheter which is guided to its intended position in the patient's cardiovascular system. Entering the femoral artery, the dilating balloon catheter is guided upwardly through the descending aorta, across the aortic arch, and down into the ascending aorta. The tip of the catheter is then inserted in the ostium of either the right or left coronary artery.

To make all of the required changes of direction within a patient's cardiovascular system, the catheter being used in the cardiovascular procedure must be capable of bending as well as twisting along its longitudinal axis as it travels through the arteries. And because it is important that the bending and twisting of the catheter not restrict the flow of liquids or gasses through any of the lumens of the catheter, nor hamper the movement of any guiding therapeutic or diagnostic means within a catheter lumen, it is important that the lumens remain unobstructed and substantially undeformed during the bending and twisting motion.

The cardiovascular application referred to above is an example of just one use for multiple lumen catheters. Multiple lumen catheters can be designed for and used in a number of other applications as well. Deformation of the lumens during manufacturing or use of multi-lumen catheters designed for a variety of uses is a problem which has faced many designers and users of the catheters.

One problem which has occurred in the construction of multiple lumen catheters is the sealing of the coaxial lumens disposed outside the central inner lumen, at the distal tip of the catheter, while at the same time keeping the outer lumens open and unobstructed. The problem occurs because balloons are frequently fastened to the outer tube of the catheter by thread winding under tension. The tensioned winding can restrict or close the outer lumen or lumens of the catheter, thereby making it difficult or impossible to inflate the balloon, if the balloon is inflated through one of the outer lumens, which is usually the preferred method for balloon inflation.

SUMMARY OF THE INVENTION

This invention relates to a multiple lumen catheter with a precisely and dependably sealed distal tip, which catheter is characterized by unobstructed lumens permitting unrestricted flow of fluids through the lumens, regardless of the bending and torque forces which are applied to the catheter during its movement through the body of the patient.

The invention further relates to a method for constructing a catheter in such a manner that the bending and torque forces applied to the catheter during its use will permit the lumens of said catheter to remain unobstructed, thereby in turn permitting the catheter to function in its intended manner.

This invention also relates to a novel means for placement between an inner and outer lumen, which means holds the inner and outer lumens in a fixed relationship to each other, while affording unobstructed passage of fluids and devices from the proximal end of the catheter through to the balloon and the catheter's distal tip.

The present invention is a multiple lumen catheter comprising
- a) a tubular member having a flexible cylindrical wall, said tubular member comprising an outer tubular body and an inner tubular body coaxially disposed within said outer tubular body, said tubular member having a proximal end portion and a distal end portion, said distal end portion terminating in a distal tip,
- b) multiple lumens extending longitudinally within the length of said tubular member, at least one inner lumen and at least one outer lumen being formed within said tubular member by said inner tubular body disposed within said outer tubular body, both tubular bodies extending along and forming at least a portion of said preformed tubular member,
- c) an opening in the wall of said outer tubular body,
- d) an inflatable member attached to said distal end portion of said tubular member at two points distal and proximal to each other along the longitudinal axis of said tubular member, and operatively associated with said outer lumen by said opening in said outer tubular body, said opening disposed within the length of outer tubular body covered by said inflatable member, and
- e) a bushing disposed between said outer and inner tubular bodies in the outer lumen formed by said bodies, said bushing having an aperture extending from a point distal to all or part of said opening in the outer tubular body to the proximal end of said bushing, said aperture being operatively associated with said opening in said outer tubular body to create a channel from the outer lumen through the bushing, through the outer tubular body, and to the interior surface of the inflatable member.

The invention also comprises a method of constructing a multiple lumen catheter comprising
- a) placing an inner tubular body within an outer tubular body to form a lumen between said tubular bodies, thereby forming a tubular member of said catheter, said lumen having a proximal and distal end, said tubular member having a proximal end portion and a distal end portion thereof, and further having a multiplicity of radially disposed coaxial lumens extending along the longitudinal axis of said tubular member, b) placing a bushing in the lumen formed between said inner and outer tubular bodies, said bushing having a proximal end and a distal end, c) heating a portion of the distal end portion of said tubular body so that the length of the bushing is positioned within the heated portion, said heating carried out at a temperature and for a time that the bushing attains plastic flow, and at a temperature and for a time to seal the distal end of said lumen, and d) attaching an inflatable member to the distal end portion of said tubular body so that the inflatable member extends both distally and proximally beyond said opening.

The invention also includes a bushing comprising a cylindrical member having a proximal and distal end thereof, an aperture having a proximal and distal edge in the circumference of said cylindrical member, said aperture extending from the proximal edge of said member to a point not reaching the distal edge of said member.

BRIEF DESCRIPTION OF THE DRAWINGS

The foregoing summary of the invention will be more fully understood by reference to the following detailed description and the accompanying drawings wherein.

DESCRIPTION OF PREFERRED EMBODIMENTS

Figure 1:
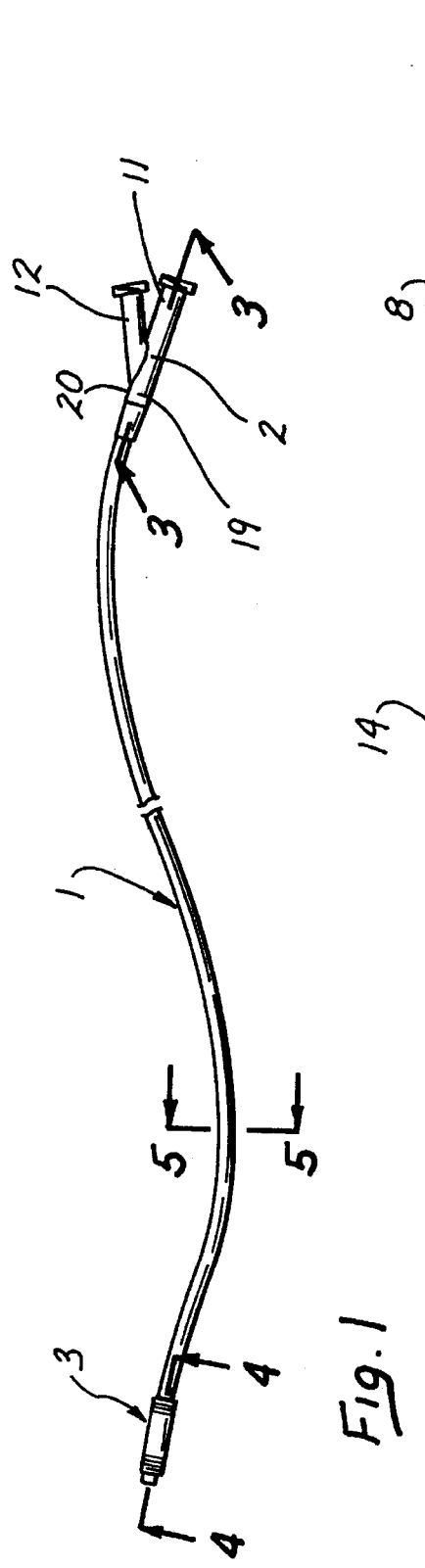
FIG. 1 is a perspective view of a catheter within the scope of this invention.
Figure 5:
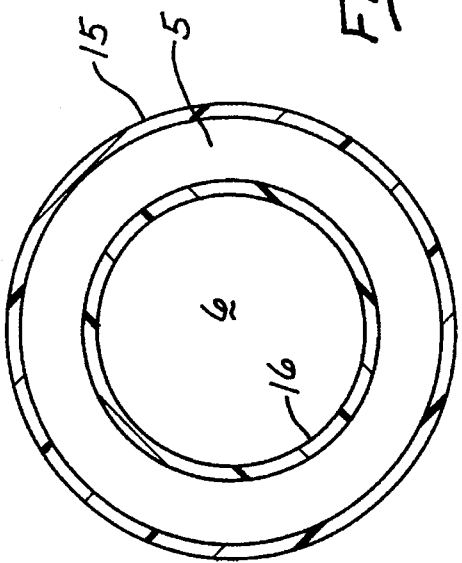
FIG. 5 is a cross-sectional view of the tubular body of the catheter of FIG. 1, taken along the line 5—5 of FIG. 1, showing the coaxial lumens of the catheter.

The present invention is embodied in a catheter 1 of the type frequently used for diagnostic or therapeutic purposes and containing multiple lumens, as shown in FIG. 1. The catheter includes a proximal end portion 2 and a distal end portion 3 connected by a tubular member 4. The tubular member 4 can have a plurality of coaxially disposed lumens 5 and 6, as shown in FIG. 5.

Figure 3:
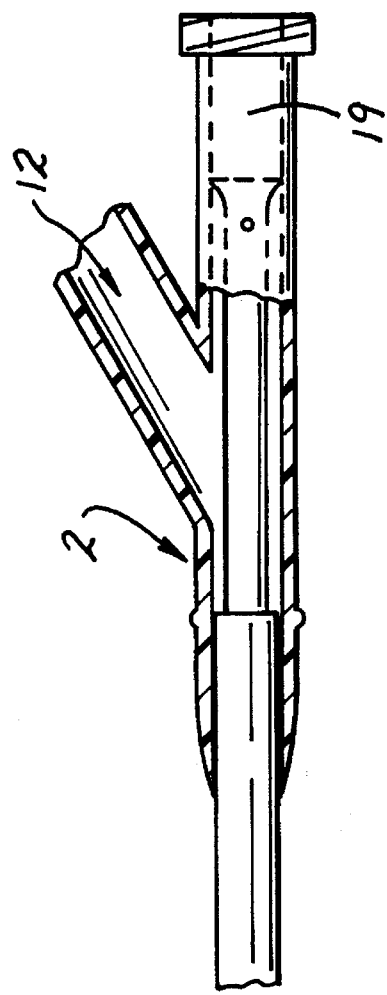
FIG. 3 is a longitudinal cross-sectional view of the proximal end portion of the catheter of FIG. 1, taken along the line 3—3 of FIG. 1.

FIG. 3 shows the proximal end portion 2 of the catheter, which includes a through lumen port 11 which is operatively connected with the through lumen 19, which extends from the proximal-most portion of the catheter to its distal-most portion. Coaxial injection point 12 is operatively connected with coaxial lumen 5 which is formed by the space between outer tubular body 15 and inner tubular body 16. The coaxially disposed lumen 5 is typically used for balloon inflation, but can also be used for irrigation, insufflation or for placement of guiding means or for other uses as well. Both the inner tubular body 16 and the outer tubular body 15 are attached to a hub or other structure 20 used to inject fluids or to hold and control the movement of other mechanisms typically associated with catheters of this type.

Figure 4:
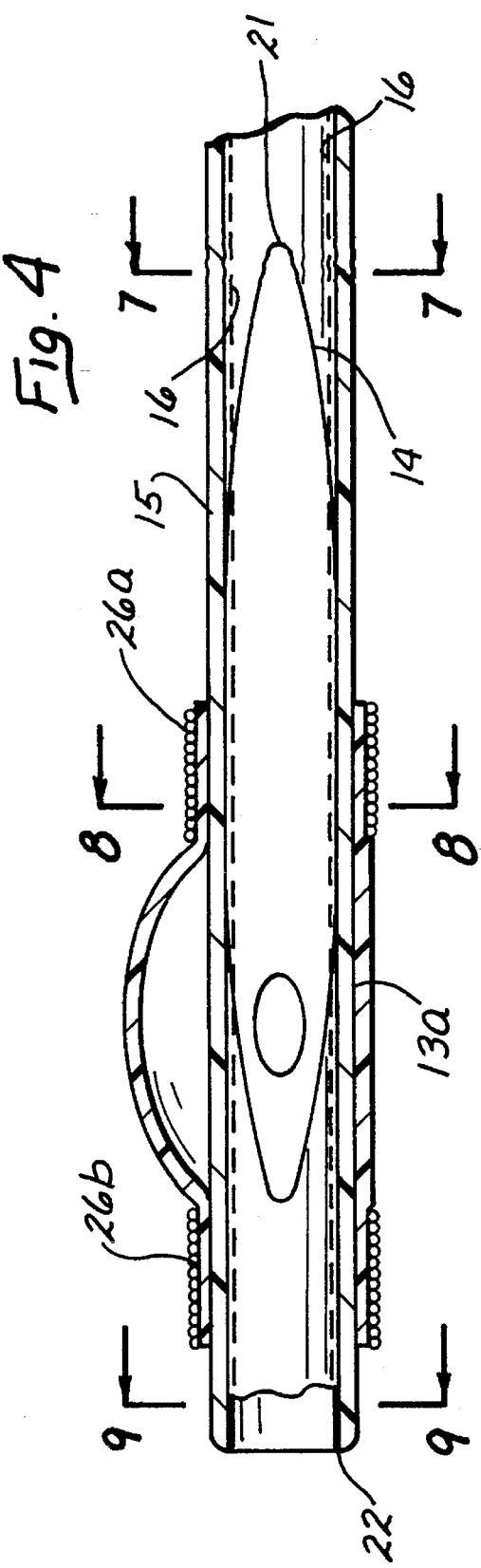
FIG. 4 is a longitudinal cross-sectional view of the distal end portion of the catheter of FIG. 1, taken along the line 4—4 of FIG. 1.

FIG. 4 is a cross-sectional view of the distal end portion of the catheter. Between outer tubular body 15 and inner tubular body 16 is disposed bushing 14. The tubular bodies 15 and 16 are sealed together with bushing 14 between them at distal tip 17. Bushing 14 extends from tip 17 along the longitudinal distance 18. The bushing 14 has an aperture 8 which extends distally beyond the opening 7 in the outer tubular body 15 and proximally to the proximal extremity of the bushing. The aperture extends sufficiently proximally that the proximal end of the bushing is not a continuous circle, but is broken by the extension of the aperture 8. The balloon 13 is formed in a preferred embodiment by a cylindrical deformable tube which is fastened to the outer body 15 by tensioned windings 26a at the proximal end and 26b at the distal end of the balloon. Balloon 13a shows the balloon in its uninflated position. The bushing extends beyond the balloon windings 26a and 26b to prevent compression and deformation of the outer and inner tubular bodies 15 and 16 at the points of potential compression of the tubular bodies by the windings 26a and 26b. The bushing preferably extends to the distal tip 17 of the tubular member. In operation of the catheter, fluid for inflation of the balloon 13 is injected through injection port 12, travels through coaxial space 5, reaches the bushing 14 and continues its passage in coaxial space 5 by passing into the aperture 8 at the proximal end of the bushing. The fluid then passes through opening 7 and inflates the balloon 13.

Catheters particularly adapted for use in the present invention because of their basic design are those referred to as through lumen catheters. A through lumen catheter is one in which one or more of the lumens within the catheter's tubular member extend from the proximal extremity of a catheter, such as depicted by injection port 11, to the distal tip, such as tip 17.

Figure 2:
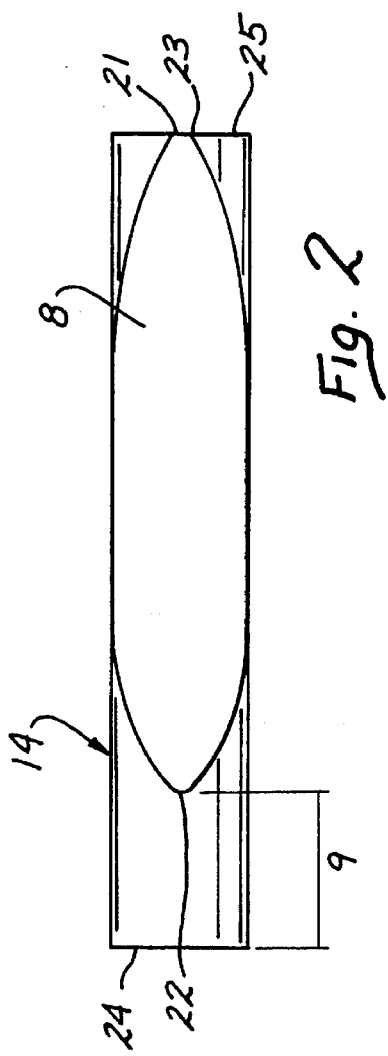
FIG. 2 is a longitudinal cross-sectional view of the bushing of this invention.

The shape and configuration of a preferred bushing can be seen in more detail in FIG. 2 where the bushing 14 has a proximal end 25 and a distal end 24. The bushing also has an aperture 8 with a proximal end 21 and a distal end 22. The proximal end 21 of the aperture extends to the proximal end of the bushing and creates a gap 23 in the proximal end circumference of the bushing shown in FIGS. 2, 7, 8, and 8a. The distal end 22 of the aperture terminates short of the distal end 24 of the bushing by a distance which is of such a length that a cylindrical tube portion 9 is created at the distal portion of the bushing 14. The aperture of the bushing is shaped in the form of an elliptical-like wedge having proximal and distal ends 21 and 22 which are tapered to somewhat pointed or needle-like ends.

Figure 8:
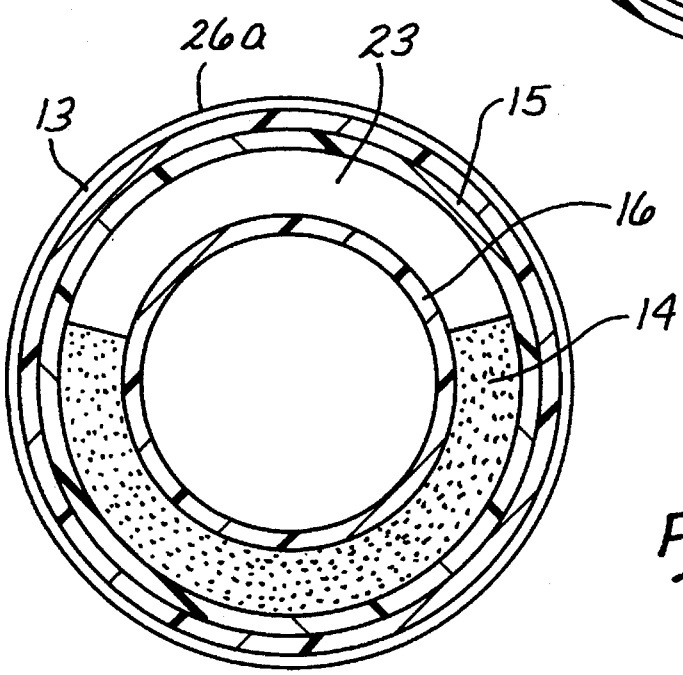
FIG. 8 is a cross-sectional view of the bushing taken through line 8—8 of FIG. 4.
Figure 8A:
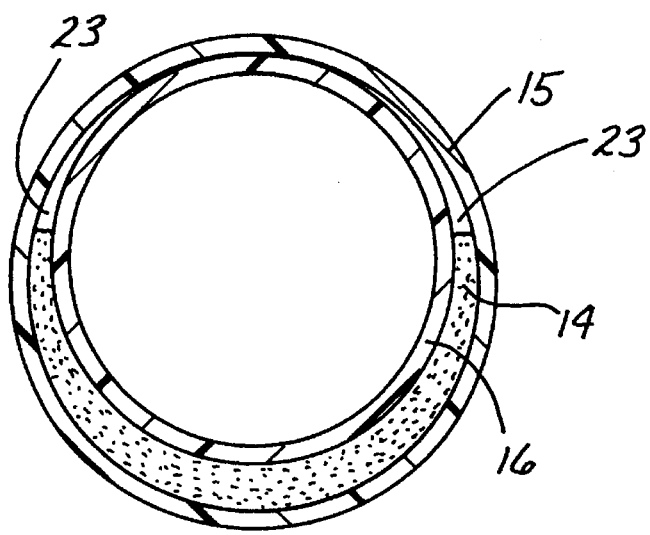
FIG. 8a is a cross-sectional view of the bushing taken through line 8—8 of FIG. 4, showing the deformation of the outer tubular member and the fluid passage maintained by the bushing.

FIG. 8 shows the wedge-like section of the bushing 14 under the proximal balloon winding 26a. FIG. 8a shows the wedge-like section of the bushing 14 under the same winding 26a and also shows the result of deformation of the outer tubular body 15 into the gap 23 positioned in the coaxial space 5. The bushing 14 assures that a portion of gap 23 remains unobstructed and provides a fluid passageway for flow from injection port 12 and opening 7.

Figure 9:
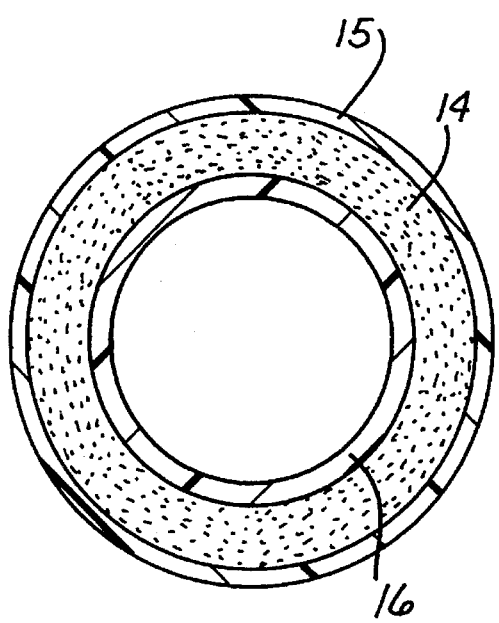
FIG. 9 is a cross-sectional view of the bushing taken through lines 9—9 of FIG. 4.

FIG. 9 shows the cylindrical portion 9 of bushing 14 in cross-section to show the sealing of outer coaxial space 5 following the heating and plastic flow of bushing 14 within the coaxial space 5.

Figure 6:
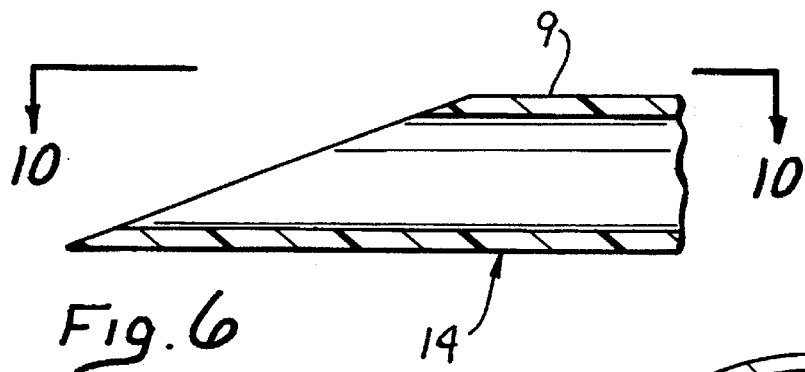
FIG. 6 is a cross-sectional view of the bushing showing the wedge shape which can be produced by shaping the aperture therein.
Figure 7:
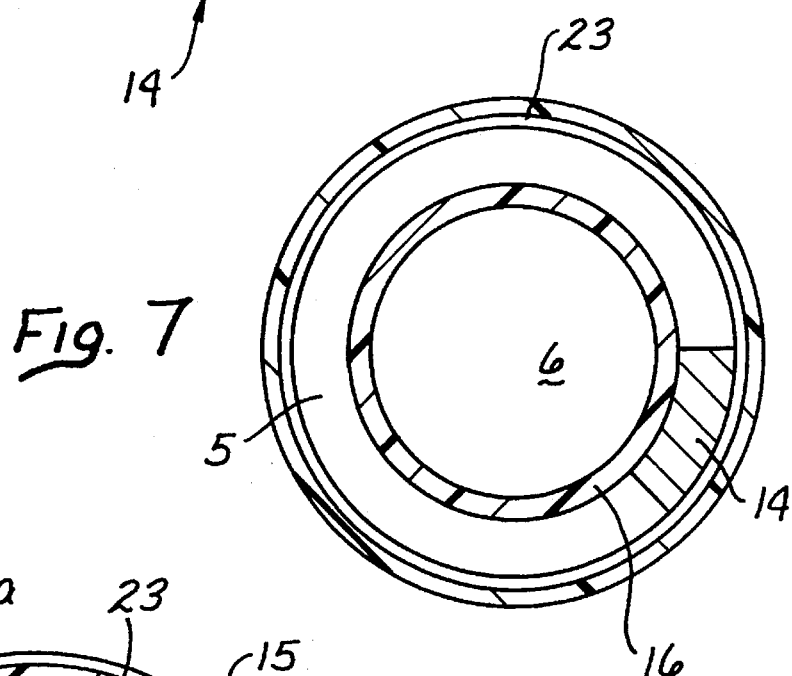
FIG. 7 is a cross-sectional view of the bushing taken through line 7—7 of FIG. 4.
Figure 10:
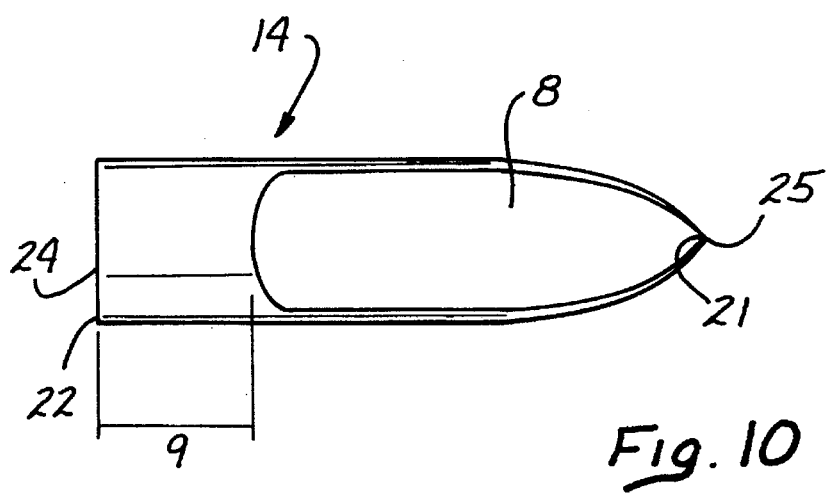
FIG. 10 is a cross-sectional view of the bushing taken through lines 10—10 of FIG. 6.

FIG. 10 is a cross-sectional view of the bushing 14 of FIG. 6 taken along line 10—10. The view shows aperture 8 with its proximal end 21 extending to bushing proximal end 25. Distal end 24 of the bushing is also shown.

The catheter of this invention is constructed as follows. The inner tubular body 16 is placed inside the outer tubular body 15 and both are sealingly attached to a hub or other structure 20 in such a manner that no leakage of gaseous or liquid fluids can occur. The positions of the two tubular bodies are such that a coaxial space 5 and an inner lumen 6 are formed. An inner lumen 6 can coincide with and be identical with a through lumen 19 if the inner lumen extends the entire length of the catheter. The distal tip 17 of the tubular member can be trimmed so that the outer and inner tubular bodies are flush with each other, or the trimming can be carried out in such a manner that either of the tubular bodies can be longer than the other. It may be advantageous for the inner tubular body to be longer than the outer body in some processes to facilitate placement of the bushing between the two bodies.

The bushing 14 is inserted into the coaxial space between the two bodies. It is preferable that the bushing be inserted between the two tubular bodies by inserting it at the distal tip 7 which is open and readily accessible. By doing so, the bushing need only be advanced a relatively short distance to reach its desired position in the distal portion of the tubular member. The bushing can also be inserted from the proximal end of the tubular member if the bushing and the inner and outer tubular bodies are of a diameter and degree of low friction which will permit the bushing to be moved through the coaxial space for a longer distance than required if the bushing were to be inserted from the distal tip.

In the broadest aspects of the method of this invention, the outer tubular body need not have an opening 7, and the bushing need not have an aperture 8. In the use of the method to construct a preferred embodiment of the invention, the outer tubular body 15 has an opening 7 within the distal end portion 3 of tubular member 4. The bushing also preferably has an aperture in a portion of its circumference extending from the edge of its proximal end 21 to a point proximal of its distal ends 22. Again in a preferred embodiment, the aperture 8 is positioned so that it surrounds the opening 7 prior to the application of heat to the bushing.

The bushing is positioned in the distal portion of the tubular member so that the bushing aperture 8 is placed over and around the opening 7 in the outer tubular body 15. The bushing, when suitably placed with respect to the other elements of the catheter, extends distally toward the tip 17 of the tubular member 4 as well as distally beyond the region where the distal balloon windings 26b will be placed along the circumference of the outer tubular body 15 and over the end of the balloon material 13 and 13a. The aperture 8 can extend into the region circumscribed by the tensioned windings 26b, but preferably does not extend into that region. The aperture 8 does extend through the region circumscribed by windings 26a and extends to the proximal end 25 of the bushing, creating a gap 23, which permits flow of fluids to continue through the coaxial space 5. The tip 17 is inserted into a heated die and the distal portion of the tubular member 4 is inserted into the die so that some length of the bushing 14 is subjected to the heat of the die. The tip is sealed and the inner lumen 6 and coaxial space 5 are also sealed in such a manner that there is no passage between lumens 5 and 6, and no passage from coaxial lumen 5 to the outside.

The tubular member is heated to such an extent that the bushing 14 exhibits plastic flow within the coaxial space 5, thereby sealing the coaxial space 5 in that region where the bushing is placed. The sealing of the space 5 gives extra rigidity and resistance to deformation to the sealed region. The degree of plastic flow need not be extensive, but only enough to produce the desired sealing and/or rigidity and resistance to deformation.

Following the heating of the distal portion of the tubular member 4, the balloon 13 or other inflatable means can be attached to the catheter by the tensioned windings or in some other suitable manner.

The bushing 14 is preferably an elongated cylinder having a height greater than its diameter, and more preferably having a height more than twice its diameter. The thickness of the bushing wall will be dictated by the coaxial space 5 of the catheter tubular member into which it will be inserted. A suitable bushing wall thickness can be approximately 0.1 to 3 mm.

The bushing can be formed of any of a variety of thermoplastic materials which are capable of exhibiting plastic flow upon being heated to some elevated temperature. For that reason, it is preferable that the plastic material of the bushing not be extensively crosslinked, which has the effect of reducing plastic flow, as well as inducing a greater degree of "memory" to the plastic article, which causes it to revert to a shape similar to its original unheated shape upon cooling.

The aperture 8 of the bushing is an important feature of the invention. The aperture is desirably elliptical having pointed ends 21 and 22 at opposite ends of the major axis of the elliptical aperture. The aperture proximal end 21 extends to the bushing proximal end 25, thereby creating a gap 23 in the circumferential end of the bushing. The reference to an elliptical shape of the aperture is not limited to shapes which conform exactly to the mathematical formula for an ellipse, but rather to shapes which approximate an elliptical shape.

Another preferred shape of the aperture in the bushing is one which produces a wedge configuration for the bushing. The wedge configuration for the bushing is shown in FIG. 6. The wedge configuration of the bushing facilitates the insertion of the bushing into the coaxial lumen and aids in its correct placement with respect to the opening in the outer tubular body and the tensioned windings used to fasten the inflatable member to the tubular member.

The aperture at its widest point preferably does not extend beyond more than half of the circumference of the bushing. In some constructions, it may be advisable to restrict the widest point of the opening, that is its minor axis if the aperture has an elliptical shape, to a width less than half the circumference of the bushing.

The aperture need not have a classic elliptical shape. The aperture distal end 22 can be circular or nearly circular in shape, as long as it permits a complete or nearly complete surrounding of the opening 7. The aperture proximal end 21, however, should extend to the bushing proximal end 25, creating a gap 23, if there is to be an unobstructed passage for fluid flow.

Catheters within the scope of the present invention can be used in a number of different diagnostic and therapeutic applications such as thrombectomy, embolectomy, irrigation, infusion, cholangiography, angiography, angioplasty, dilatation, dilation, tissue planing, hystero-salpingography, and a number of diagnostic procedures.

It is recognized that a number of variations in the catheter designs are within the scope of this invention. For example, a balloon has been discussed as an inflatable means comprising a part of this inventive catheter design. Other inflatable shapes could also be used herein. The balloon is shown attached at its distal end at a point proximally located from the distal tip 17. The balloon could be positioned so that the distal-most portion of the balloon is fastened within the distal tip, thereby creating a balloon positioned on the very end of the tubular member. Such a placement would be included within this invention.

There are a number of adjunctive devices which can be used advantageously with the catheters of this invention. Fiber optic bundles can be run through either of the lumens to illuminate the passages through which the catheter is moving, either with or without a camera lens or body. The multiple lumens of a catheter need not be coaxially disposed with respect to one another. The lumens can instead be placed parallel to and outside one another within a larger tubular body which holds all of the lumens separate from the others. In such an embodiment the present invention can also be advantageously used to sealingly engage one or more of the tubular bodies within the tubular member. These and other modifications can be made within the scope of this invention.

What is claimed is:

1. A multiple lumen catheter comprising
   a) a tubular member having a flexible cylindrical wall, said tubular member comprising an outer tubular body and an inner tubular body coaxially disposed within said outer tubular body, said tubular member having a proximal end portion and a distal end portion, said distal end portion terminating in a distal tip,
   b) multiple lumens extending longitudinally within the length of said tubular member, at least one inner lumen and at least one outer lumen being formed within said tubular member by said inner tubular body disposed within said outer tubular body, both tubular bodies extending along and forming at least a portion of said tubular member,
   c) an opening in the wall of said outer tubular body,
   d) an inflatable member attached to said distal end portion of said tubular member at multiple points distal and proximal to one other along the longitudinal axis of said tubular member, and operatively associated with said outer lumen by said opening in said outer tubular body, said opening disposed within the length of outer tubular body covered by said inflatable member, and
   e) a bushing disposed between said outer and inner tubular bodies in the outer lumen formed by said bodies, said bushing having an aperture extending from a point distal to at least a portion of said opening in the outer tubular body to the proximal end of said bushing, said aperture being operatively associated with said opening in said outer tubular body to create a channel from the outer lumen through the bushing, through the outer tubular body, and to the interior surface of the inflatable member.

2. A catheter according to claim 1 where said catheter is a cardiovascular catheter.

3. A catheter according to claim 1 where said catheter is used in performing a hystero-salpingography procedure.

4. A catheter according to claim 1 where said bushing extends to a point distally beyond the distal point of attachment of said inflatable member.

5. A catheter according to claim 1 where said aperture in said bushing does not extend distally to the distal point of attachment of said inflatable member.

6. A catheter according to claim 1 where said aperture in said bushing is circumferentially wider at the point where it circumscribes the opening in the outer tubular body than it is at the proximal end of said bushing.

7. A catheter according to claim 1 where said inflatable member is a balloon.

8. A catheter according to claim 1 where said bushing is positioned on the longitudinal axis of said tubular member so that said bushing extends from a point distally beyond the distal point of attachment of said inflatable member to said tubular member, and proximally beyond the proximal point of attachment of said inflatable member to said tubular member.

9. A catheter according to claim 1 where said outer and inner tubular bodies terminate flush with each other in the distal tip.

10. A catheter according to claim 1 wherein said bushing extends from a point distally beyond the distal point of attachment of said inflatable member to said tubular member, and proximally beyond the proximal point of attachment of said inflatable member to said tubular member, and where said outer and inner tubular bodies and said bushing are flush with one another at the distal tip of said tubular member.

11. A method of constructing a multiple lumen catheter comprising
    a) placing an inner tubular body within an outer tubular body to form a lumen between said tubular bodies, thereby forming a tubular member of said catheter, said lumen having a proximal and distal end, said tubular member having a proximal end portion and a distal end portion thereof, and further having a multiplicity of radially disposed coaxial lumens extending along the longitudinal axis of said tubular member,
    b) placing a bushing in the lumen formed between said inner and outer tubular bodies, said bushing having a proximal end and a distal end,
    c) heating the distal end portion of said tubular body and the bushing to a temperature sufficient that the bushing attains plastic flow, and for a time sufficient to seal the distal end of said lumen, and
    d) attaching an inflatable member to the distal end portion of said tubular body so that the inflatable member extends both distally and proximally of said opening.

12. A method according to claim 11 wherein said outer tubular body has an opening in its surface which is positioned within the distal end portion of said tubular member, and wherein said bushing has an aperture in a portion of its circumference extending from the edge of its proximal end to a point not coextensive with the edge of its distal end, said aperture being positioned so that it surrounds said opening.

13. A method according to claim 11 wherein said inflatable member is attached to said outer tubular body so that the inflatable member does not extend proximally beyond the proximal end of said bushing member.

14. A method according to claim 11 wherein said outer and inner tubular bodies are placed flush with each other in the distal end of said lumen before said distal end portion is heated to seal the distal end of said lumen.

15. A bushing adapted for use in a multiple lumen catheter comprising a cylindrical member having a proximal end and distal end, a portion of the cylindrical member defining an aperture having a proximal and distal edge in the circumference of said cylindrical member, said aperture extending from the proximal end of said member to a point proximal of the distal end of said member.

16. A bushing according to claim 15 wherein said aperture is elliptical in shape.

17. A bushing according to claim 15 wherein the proximal and distal edges of said aperture are pointed in shape.

18. A bushing according to claim 15 wherein the aperture is tapered from a point approximately coincidental with the opening to the proximal edge of said member to produce a wedge shape of the member.

19. A bushing according to claim 15 where the length of the cylindrical member is at least twice the diameter of said member.

* * * * *